US00PP18728P3

(12) United States Plant Patent
Rumbal

(10) Patent No.: US PP18,728 P3
(45) Date of Patent: Apr. 15, 2008

(54) JAPANESE MAPLE PLANT NAMED 'GWEN'S ROSE DELIGHT'

(50) Latin Name: *Acer palmatum*
Varietal Denomination: Gwen's Rose Delight

(76) Inventor: James Palmer Rumbal, Matarikoriko Road, Waitara (NZ)

( * ) Notice: Subject to any disclaimer, the term of this patent is extended or adjusted under 35 U.S.C. 154(b) by 0 days.

(21) Appl. No.: 11/479,118

(22) Filed: Jun. 30, 2006

(65) Prior Publication Data

US 2008/0005817 P1 Jan. 3, 2008

(51) Int. Cl.
*A01H 5/00* (2006.01)

(52) U.S. Cl. ..... Plt./224
(58) Field of Classification Search ..... Plt./224
See application file for complete search history.

(56) References Cited

U.S. PATENT DOCUMENTS

PP15,943 P2 * 9/2005 van der Maat ..... Plt./224

* cited by examiner

*Primary Examiner*—Kent Bell
*Assistant Examiner*—S. B. McCormick-Ewoldt
(74) *Attorney, Agent, or Firm*—Greenlee Winner and Sullivan, PC

(57) ABSTRACT

The invention is a new variety of Japanese Maple. The variety is a robust tree with a leaf color predominantly green/purple with a pale pink to white margin.

7 Drawing Sheets

Genus and species of plant claimed: *Acer palmatum.*
Variety denomination: 'Gwen's Rose Delight'.

BACKGROUND OF THE INVENTION

The term "Japanese Maple" mainly refers to varieties of *Acer palmatum* and its close relatives.

Japanese maple plants are valued for being decorative outdoor trees. Many varieties of Japanese maple are suitable for being maintained at a small size and to fit into a small space. Japanese maples are often a source of interesting color for a garden.

The present variety arose as a sport from a plant of *Acer palmatum* 'Geisha' (non-patented). This discovery was made at 90 Waitara Rd, Brixton, New Plymouth, New Zealand in the summer of 2001. Eight growth buds were removed from the originally observed plant and these were reproduced via asexual propagation via bud grafting onto *Acer palmatum* rootstock (a non-patented variety) in New Plymouth, New Zealand. These eight buds came into growth approximately six months later in spring and were observed to be true to the original plant. From this original propagation further bud grafts were made during following propagation seasons of January to February and the stock was increased incrementally as propagation material became available. Throughout this period the plants were observed to be true to the original parent plant. This further propagation took place at 109 Waitara Road, Brixton, New Plymouth, New Zealand.

SUMMARY OF THE INVENTION

The present variety is a robust tree with a leaf color predominantly green/purple with a pale pink to white margin.

This variety is typically propagated by means of asexual bud grafting during summer. Growth is observed during the following spring typically 5–6 months later.

BRIEF DESCRIPTION OF THE DRAWINGS

The accompanying photographs show typical specimens of the new variety as depicted in colors as true as is reasonably possible to make the same color illustration of this character.

DETAILED DESCRIPTION

Figure 1:
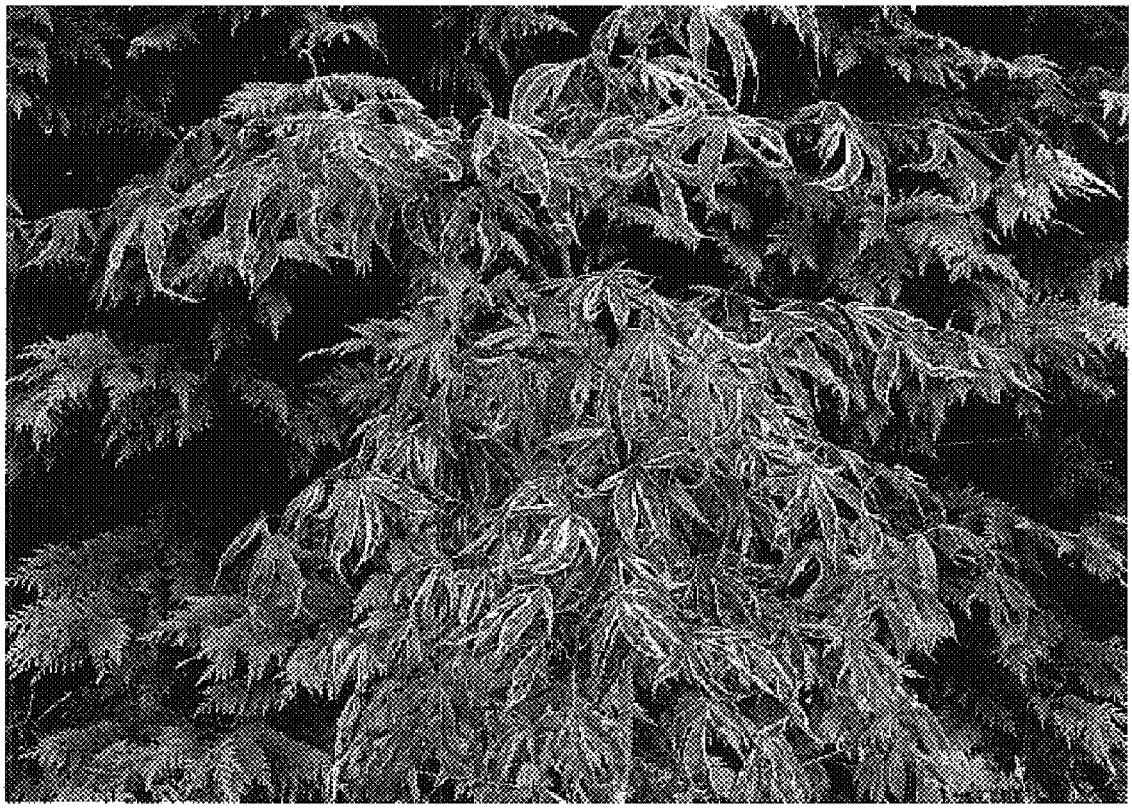
FIG. 1: single stem in summer.
Figure 2:
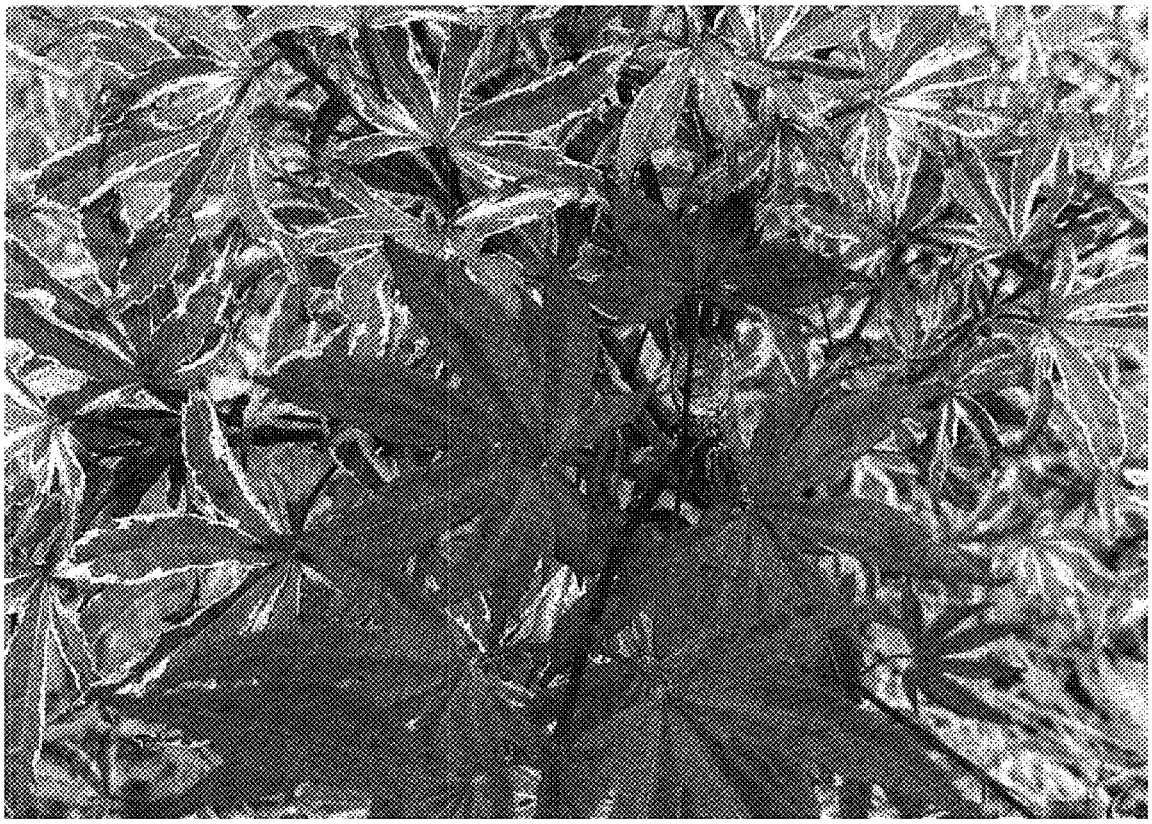
FIG. 2: foliage now growth (redder coloration) on old.
Figure 3:
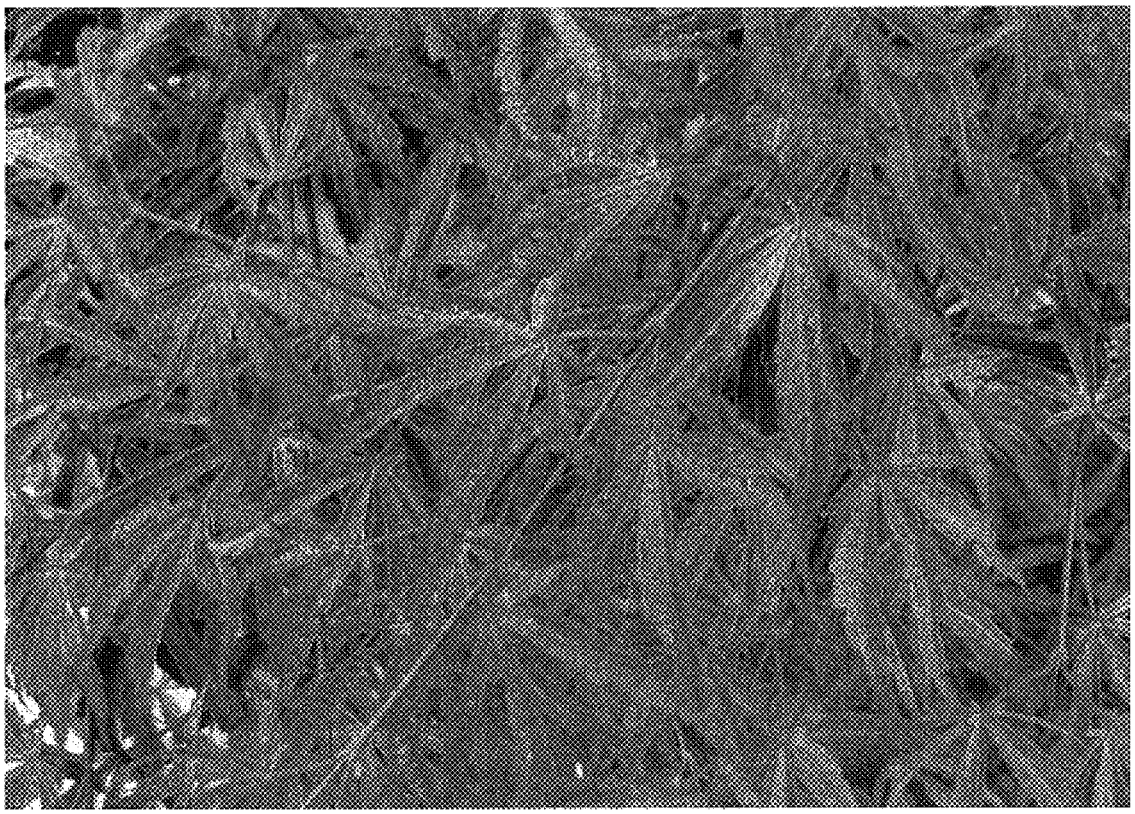
FIG. 3: new foliage in summer.
Figure 4:
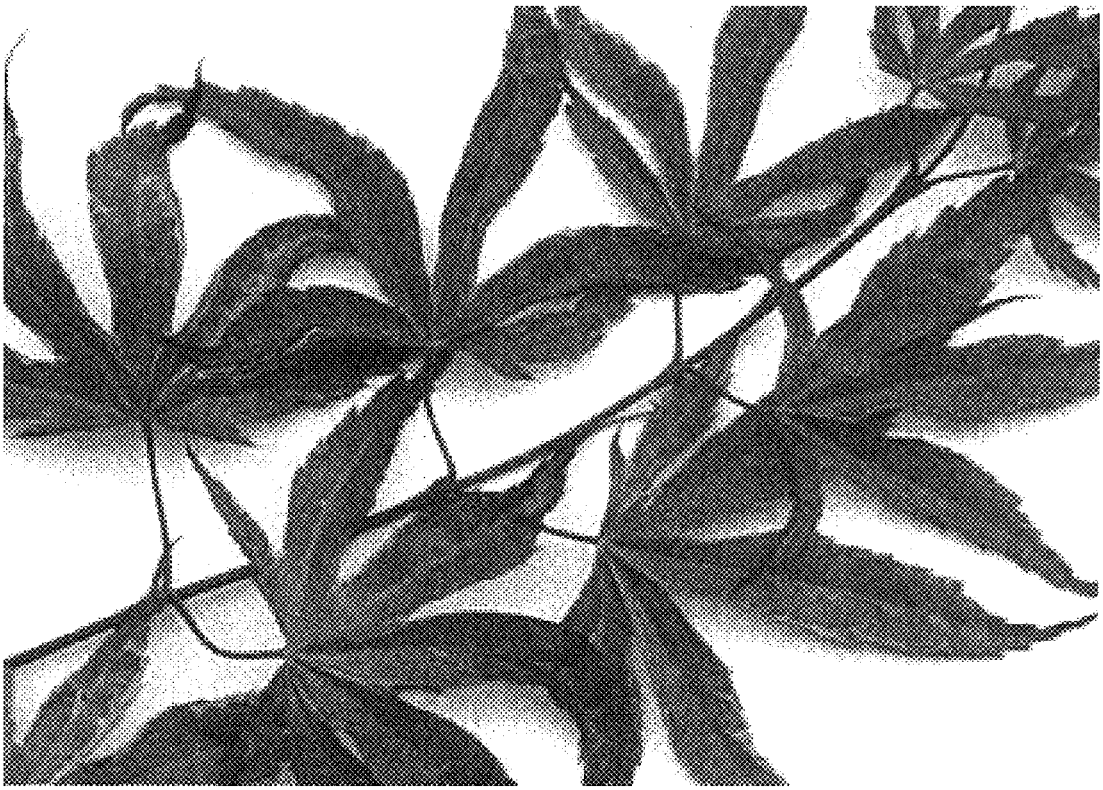
FIG. 4: early summer leaves.
Figure 5:
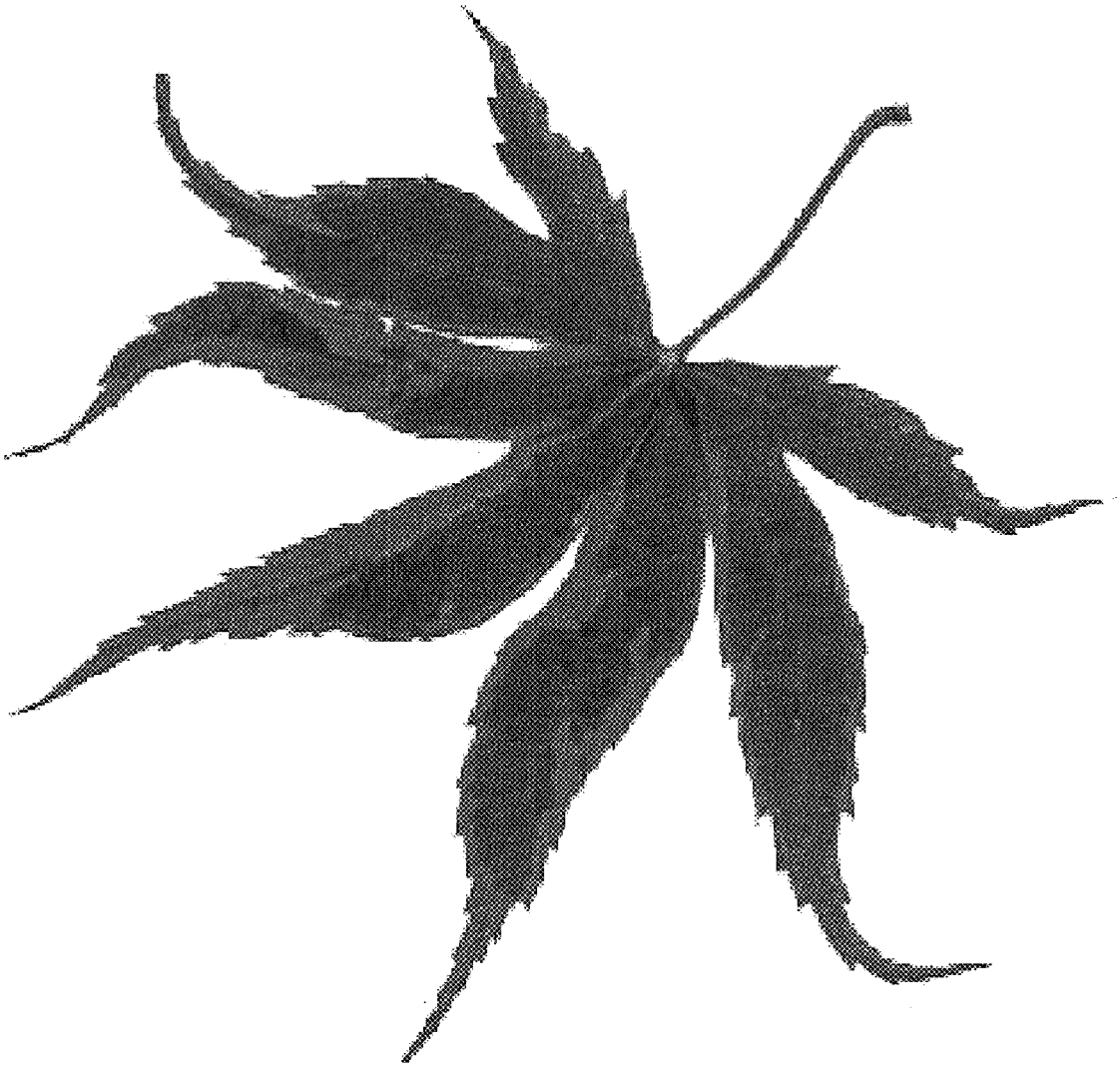
FIG. 5: early summer leaf.
Figure 6:
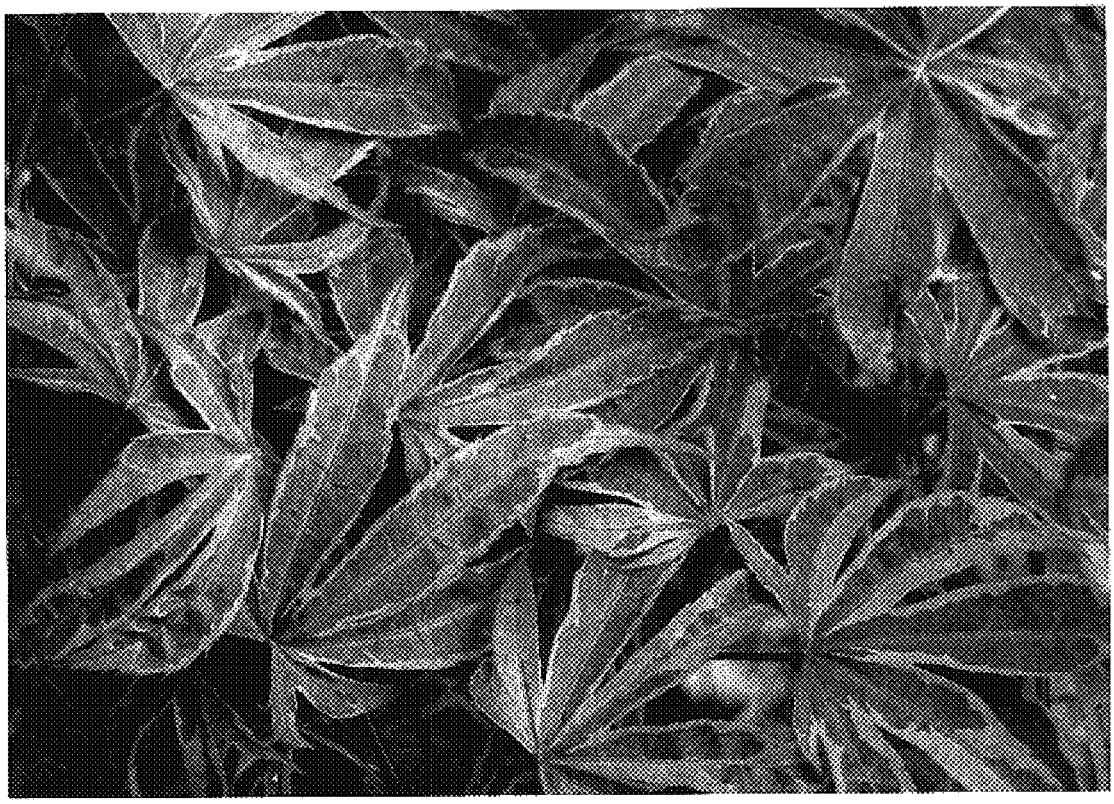
FIG. 6: early summer leaves.
Figure 7:
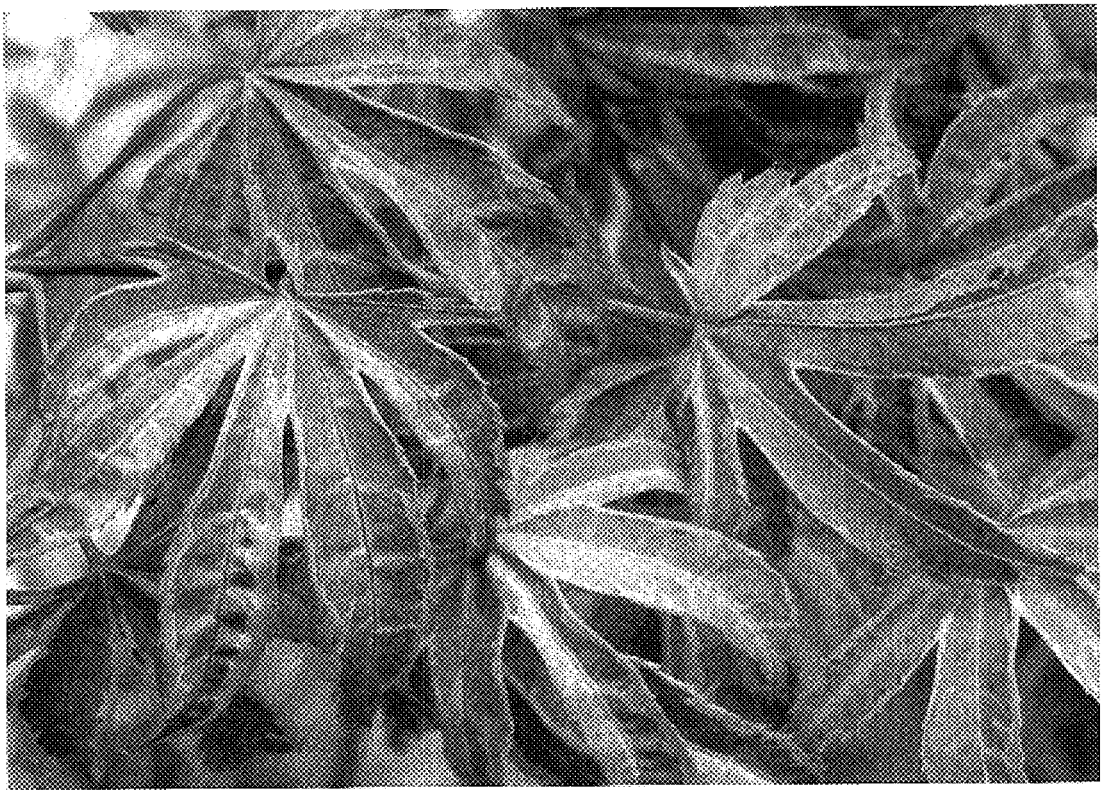
FIG. 7: early summer leaves.

The following description is based on observations of two year old plants in 2005. The site was 90 Waitara Road, Brixton, New Plymouth. The plants were propagated by grafting of buds onto *Acer palmatum* seeding rootstock.

Colors are described using The Royal Horticultural Society Colour Chart (RHS).

Plants:

At two years old (trimmed) the plant has a height of 1.2 m. The approximate ultimate height is 4–6 meters with a spread of approximately 2–3 meters and a mature trunk diameter at 30 centimeters above ground level of approximately 20 centimeters to 30 centimeters. The branch system is semi-erect.

Trunk & Branch:

The trunk/bark color is Greyed-Orange 176A and Yellow-Green 146C. The branch color in winter is Greyed-Purple 187A with an overlying stem bloom of White 155C. Pubescence is absent.

*Lenticels.*—White present, are not a distinct feature of this plant.

In a mature specimen the tree is many branched, forming a full, round headed small tree. In a juvenile specimen the branches are upright with semi-pendulous tips becoming more upright as the tree ages. Annual spring flush on a juvenile plant appears to be 30 to 80 centimeters slowing to approximately 20 to 30 centimeters on a mature specimen. Internode length on spring flush is observed as 3 to 6 centimeters. Diameter is observed as 3 to 5 millimeters. On a mature specimen branch diameter is observed as 1 to 3 centimeters.

Leaf arrangement and form:

*Foliage arrangement.*—Opposite, simple.

*Leaf shape.*—Palmate, five and occasionally seven part. Apex acute. Lobes are slender of 8–15 millimeters width at the widest point. Margins are serrate. Texture of upper and lower surfaces is smooth and without pubescence.

*Leaf length.*—Approximately 6 to 8 centimeters excluding petiole.

*Leaf width.*—Approximately 5 to 10 centimeters.

Petioles:

*Petiole color.*—Red 45B summer, Red 45C autumn.

*Petiole length.*—3 to 4 centimeters.

*Petiole diameter.*—Approximately 1 millimeter.

Leaf colour:

*Color of summer leaf* (*young*):

*Upper surface center.*—Red — Purple 59B.

*Upper surface margin.*—Red — Purple 61C.

*Lower surface center.*—Red — Purple 59B.

*Lower surface margin.*—Red — Purple 61C.

Colour of summer leaf (mature):

*Upper surface.*—Upper surface center Yellow — Green 148D tinged with Red — Purple 71A. Central color is also irregularly flecked with grey/green patches 2–5 millimeters in diameter, colored Yellow — Green 148B. Margin Red 56B and Red 56D.

*Lower surface.*—Lower surface center Yellow — Green 148D tinged with Red — Purple 71A. Central color is also irregularly flecked with grey/green patches 2–5 millimeters in diameter, colored Yellow — Green 148B. Margin Red 56B and Red 56D.

Colour of autumn leaf:

*Upper surface.*—Red 44C and Red 40B, marginal variegation is indistinct in autumn.

*Lower surface.*—Red 44C and Red 40B, marginal variegation is indistinct in autumn.

Venation pattern:

*Venation pattern.*—Palamate.

*Venation color.*—Green — White 157C and Orange — Red 35C in spring, summer changing to Red 45A in autumn.

Other leaf characteristics: Pubescence is absent. The leaves are not glaucose. Marginal variegation is strongly evident as described in color descriptions.

Flowering:

*Flower development.*—Flowers are insignificant, this variety has been observed to set seed. Seed has not been germinated.

Temperature tolerance:

Observation of this variety has taken place in a temperate climate only. There is the expectation that this variety will perform in a manner similar to other known variegated *Acer palmatum* varieties in extremes of temperature. This variety has been observed to retain distinct foliage coloration during summer months though periods of extreme drought have not been experienced.

Resistance to pathogens:

Not noted as resistant to any pathogens and pests known to Japanese Maples.

Comparison:

The variety was compared with 'Geisha,' 'Butterfly' and 'Beni Schishihenge' (non patented varieties). 'Geisha' had a different form with spotted variegations. The leaves of 'Butterfly' were smaller and greener with no pink/red colouration. 'Beni Schishihenge' has a smaller leaf with irregular salmon pink margins. In the present variety the leaf colour which is predominantly green/purple with pale pink to white margin. The leaf is larger and the plants are taller with a more robust habit.

I claim:

1. A new and distinct Japanese Maple tree as herein illustrated and described.

* * * * *